United States Patent [19]

Penco et al.

[11] 4,067,969

[45] Jan. 10, 1978

[54] ANTHRACYCLINE GLYCOSIDES, THEIR PREPARATION AND USE

[75] Inventors: Sergio Penco; Federico Arcamone; Aurelio di Marco, all of Milan, Italy

[73] Assignee: Societa Farmaceutici Italia S.p.A., Milan, Italy

[21] Appl. No.: 722,689

[22] Filed: Sept. 13, 1976

[30] Foreign Application Priority Data

Sept. 26, 1975 United Kingdom ............... 39471/75

[51] Int. Cl.² ....................... A61K 31/70; C07H 15/24
[52] U.S. Cl. .......................................... 424/180; 536/4; 536/17; 536/18; 536/53; 536/118; 536/119; 536/122
[58] Field of Search ....................... 536/4, 17; 424/180

[56] References Cited

U.S. PATENT DOCUMENTS

| | | | |
|---|---|---|---|
| 3,697,652 | 10/1972 | Rovati et al. | 536/18 |
| 3,803,124 | 4/1974 | Arcamone et al. | 536/17 |
| 4,020,270 | 4/1977 | Arcamone et al. | 536/4 |

Primary Examiner—Johnnie R. Brown
Attorney, Agent, or Firm—Hubbell, Cohen, Stiefel & Gross

[57] ABSTRACT

The novel compounds, 4'-deoxy-daunomycin and 4'-deoxy-adriamycin, as well as derivatives thereof are useful as anti-tumor antibiotics. These compounds are prepared by condensing the corresponding aglycone with a novel trifluoracetyl protected reactive halo sugar which is 2,3,4,6-tetradeoxy-3-trifluoroacetamido-L-threo-hexopyranosyl chloride.

22 Claims, No Drawings

ANTHRACYCLINE GLYCOSIDES, THEIR PREPARATION AND USE

BACKGROUND OF THE INVENTION

1. Field of the Invention

The present invention relates to novel antitumor glycosides of the anthracycline series, which are derivatives of the known antitumor glycosides daunomycin and adriamycin, as well as their preparation and their use in treating mammalian tumors. The invention also relates to certain novel intermediates used in preparing the glycosides of the invention.

2. The Prior Art

Daunomycin and adriamycin are known antitumor antibiotics which are described and claimed in British Pat. Nos. 1,033,383 and 1,161,278 and 1,217,133, respectively, all of which are owned by the unrecorded assignee hereof.

SUMMARY OF THE INVENTION

In accordance with one aspect of the present invention, there is provided a new class of anthracycline glycoside antibiotics which are 4'-deoxy-daunomycins and 4'-deoxy-adriamycins.

In another aspect, the invention provides a new process for preparing these antibiotics.

In a further aspect, the invention provides certain novel intermediates used in the new process.

In yet another aspect, the invention provides a method of using the novel antibiotics in the treatment of various forms of mammalian tumors.

The new anthracycline glycoside antibiotics of the invention are compounds of the formula of (IV) and (XII)

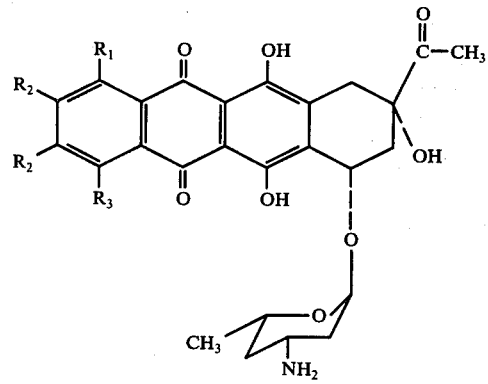

(IV)

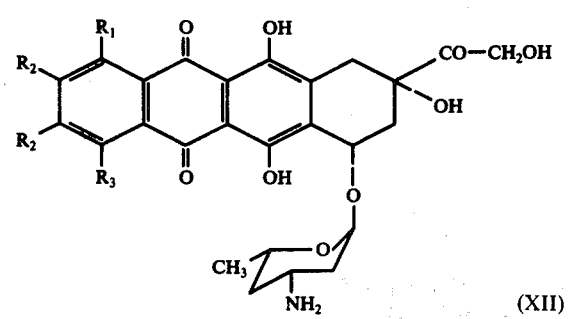

(XII)

wherein, when $R_1$ and $R_3$ are hydrogen, $R_2$ is hydrogen, methyl, methoxy, chlorine or bromine; when $R_1$ and $R_2$ are hydrogen, $R_3$ is a $C_1$–$C_4$ alkoxy group; and when $R_2$ is hydrogen, $R_1$ and $R_3$ are both methyl, methoxy, chlorine or bromine.

The new anthracycline glycoside antibiotics (IV) of the invention are condensation products of (a) a tetracyclic aglycone having a hydroxy-anthraquinone chromophoric system of the formula:

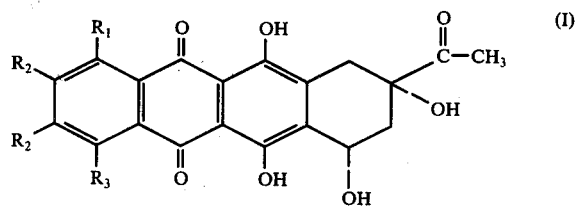

wherein $R_1$, $R_2$ and $R_3$ are as defined above and (b) the novel halo sugar: 2,3,4,6-tetradeoxy-3-trifluoroacetamido-L-threo-hexopyranosyl chloride:

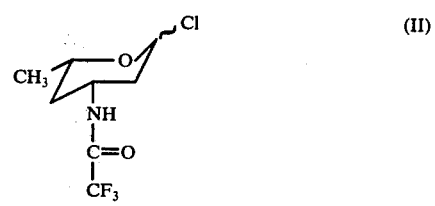

After the condensation reaction, the protecting trifluoroacetyl group (—COCF$_3$) is removed under alkaline conditions to obtain (IV) as the final product.

The process for preparing the novel compounds of formula (IV) involves a condensation reaction between aglycone (I) and halo sugar (II), which is carried out in an inert organic solvent such as chloroform, methylene dichloride, diethyl ether, tetrahydrofuran, acetonitrile, or dimethylformamide in the presence of a soluble silver salt, such as silver trifluoromethan sulphonate, as a catalyst. A dehydrating agent such as a molecular sieve is preferably also present in the reaction mixture.

The new anthracycline glycoside antibiotics (XII) of the invention are prepared by reacting a compound of the formula (IV) with bromine to obtain the 14-bromo-derivative thereof which is then hydrolyzed with sodium formate to form a compound of formula (XII) which may then be isolated as the hydrochloride.

The novel intermediates which comprise a further aspect of the invention are the following compounds of the formulae (VI), (VII), (VIII), (IX), (IXa) and (II), the latter compound being the halo sugar which is the starting material for the preparation of (IV).

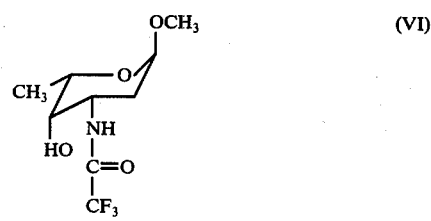

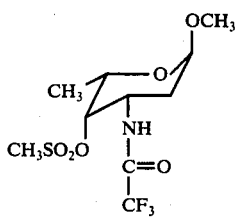

(VII)

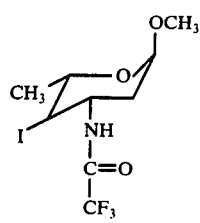

(VIII)

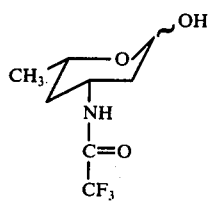

(IX)

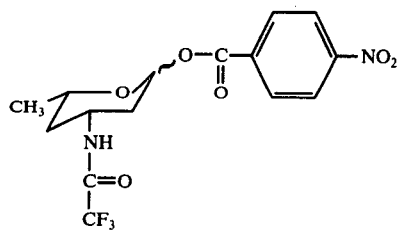

(IXa)

All of these intermediates are amino sugars of which the progenitor, i.e., the basic, unsubstituted amino sugar is 3-amino-2,3,4,6-tetradeoxy-L-threo-hexose:

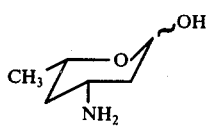

(V)

This amino sugar (V) was also previously unknown and may be obtained as its N-trifluoroacetyl derivative (IX) from methyl-N-trifluoroacetyl-daunosaminide (VI).

According to the invention, halo sugar (II) is prepared, starting from methyl-N-trifluoroacetyl-daunosaminide (VI). Compound (VI) is reacted in dry pyridine with methane sulphonyl chloride and thereby converted in a quantitative yield to its 4-O-mesyl-derivative (VII), which by treatment with sodium iodide in methylethylketone leads to the 4-iodo-derivative (VIII).

Catalytic hydrogenation of compound (VIII) followed by acid hydrolysis of the resulting methyl glycoside, yields 2,3,4,6-tetradeoxy-3-trifluoroacetamido-L-threo-hexopyranose (IX). Treatment of this intermediate (IX) with p-nitrobenzyl chloride in dry pyridine gives the corresponding 1-p-nitrobenzoate (IXa), which upon treatment at 0° C with dry hydrogen chloride in anhydrous methylene dichloride yields the desired 2,3,4,6-tetradeoxy-3-trifluoroacetamido-L-threo-hexopyranosyl chloride (II).

When in the aglycone of formula (I), $R_1 = R_2 = H$ and $R_3$ is methoxy, 4'-deoxy-daunomycin is finally obtained and isolated as its hydrochloride. Subsequent treatment in accordance with the procedures described in U.S. Pat. No. 3,803,124 yields 4'-deoxyadriamycin which is also isolated as its hydrochloride.

The novel compounds of the formula (IV) and (XII) exhibit antimitotic activity, and thus are useful in treating certain mammalian tumors.

DESCRIPTION OF THE PREFERRED EMBODIMENTS

The following examples are given to illustrate the invention without, however, being a limitation thereof. All parts given are by weight, unless otherwise indicated.

EXAMPLE 1

Preparation of the intermediate 2,3,4,6-tetradeoxy-3-trifluoroacetamido-L-threo-hexopyranosyl chloride (II)

5.2 g of methyl N-trifluoroacetyl daunosaminide (VI), dissolved in 40 ml of anhydrous pyridine, were treated at $-5°$ C with 8 ml of methane sulphonyl chloride. The reaction mixture was kept overnight at 4° C and then evaporated to a residue under vacuum. The resulting residue was dissolved in 300 ml of chloroform and washed with water until the water was neutral. The organic phase was dried over anhydrous sodium sulphate and then evaporated to yield 4.2 g of the crystalline 4-O-mesyl-derivative (VII) m.p. 169°-170° C; $[\alpha]_D -160°$ (c = 0.1 in $CHCl_3$); m/e 304 (M—$OCH_3$); PMR ($CDCl_3$—DMSO-$d_6$ 4:1) : 1.26$\delta$ (d, J = 6.5 Hz, $CH_3$—C-5), 3.18$\delta$ (s, $CH_3OSO_2$), 3.38$\delta$ (s, $CH_3O$), 4.80$\delta$ (broad s, $W_H$ = 5.5 Hz, C—1H).

8.7 g of the dried compound (VII) were dissolved in 150 ml of methylethylketone, treated with 5 g of sodium iodide and heated at reflux temperature for 24 hours. The reaction mixture was evaporated to a residue which was then suspended in 200 ml of chloroform. The insoluble material was filtered off, and the organic phase was washed with a 3% aqueous sodium thiosulphate solution and then with water. The washed organic phase was evaporated to a residue under vacuum to yield a crude product. The crude product was purified by chromatography on a column of silicic acid using benzene : acetone (20:1) as the eluent. There were obtained 2.3 g of crystalline compound (VIII) m.p. 194°-195° C; $[\alpha]_D - 100°$ (c = 0.1 in $CHCl_3$); m/e 367 (M+); PMR ($CDCl_3$—DMSO-$d_6$2:1) : 1.46 $\delta$ (d, J = 6.0 Hz, $CH_3$—C-5), 3.38$\delta$ (s, $CH_3O$) and 4.83$\delta$ (dd, J=2.5 Hz, C—1H).

2.3 g of compound (VIII) were dissolved in 80 ml of methanol and hydrogenated under pressure (15 atm) at room temperature for 62 hours in the presence of 4 g of barium carbonate and 4 g of 10% palladium on charcoal. The catalyst was filtered off and the organic solution (methanol) was evaporated to a residue. The resulting residue (1 g) was suspended in 100 ml of chloroform and the insoluble material was filtered off. The solution was then evaporated, and the resulting residue was dissolved in 20 ml of water to which was added 5 ml of glacial acetic acid. The solution was heated for 3 hours at 90° C to evaporate off the solvents and yield crystalline compound (IX) in quantitative yield m.p. 159°-160° C; at equilibrium $[\alpha]_D^{20} = -80°$ (c = 0.1 in $CHCl_3$); m/e 210 (M—OH); PMR (DMSO-$d_6$) : 1.03$\delta$ (d, J = 6.0

Hz, $CH_3$-C-5 α-anomer), 1.09δ (d, J = 6.0 Hz, $CH_3$-C-5 β-anomer), 1.2–1.9δ (m, C-2$H_2$ e C—4$H_2$), 4.60δ (dd, J = 2.0 Hz, J' = 9 Hz, C-1 Hax), 5.17δ (broad s, w$_H$ 6Hz, C-1 Heq.).

To a solution of 1 g of compound (IX) in 10 ml of anhydrous pyridine, 2 g of p-nitrobenzoyl chloride were added. After 12 hours at room temperature, the reaction mixture was poured onto ice and the resulting precipitate was washed with water until the water was neutral. The resulting crude 1-p-nitrobenzoate (mixture of α and β anomer) was dried over phosphorus pentoxide for several hours under vacuum, and then dissolved in dry methylene dichloride and saturated at 0° with anhydrous hydrogen chloride. The precipitated p-nitrobenzoic acid was filtered off under anhydrous conditions, and the 1-chloro derivative (II) was obtained in quantitative yield by evaporation of the solvent. Compound (II) can be used for the ensuing condensation reaction without further purification.

EXAMPLE 2

4'-deoxy-daunomycin

A solution of 1.5 g of daunomycinone in 150 ml of anhydrous methylene dichloride containing 0.75 g of 2,3,4,6-tetradeoxy-3-trifluoroacetamido-L-threo-hexopyranosyl chloride (II), was vigorously stirred in the presence of 10 g of molecular sieve (4 A Merck) and 0.77 g of $AgSO_3CF_3$ in 20 ml of anhydrous diethyl ether. After two hours at room temperature, the reaction mixture was neutralized with a saturated aqueous solution of sodium bicarbonate and the organic phase, after being separated, was evaporated under vacuum to obtain a residue. The thus obtained residue was dissolved in 50 ml of 0.1 N aqueous sodium hydroxide, and after 30 minutes at 0° C the solution was adjusted to pH 3.5 and repeatedly extracted with chloroform to eliminate the unreacted aglycone. Then the solution was ajusted to pH 8.3 and extracted with chloroform until the chloroform extracts were no longer colored. The chloroform extracts were combined, dried over anhydrous sodium sulphate and concentrated to a small volume and thereafter acidified to pH 4.5 with 0.1 N methanolic hydrogen chloride. The addition of excess diethyl ether yielded 4'-deoxydaunomycin as the hydrochloride; m.p. 160°–164° C (dec). A sample of the product was subjected to thin layer chromatography (TLC) on Merck Kieselgel $F_{254}$ plates using a chloroform-methanol-water (150 : 42 : 6 v/v) solvent system. The Rf of the compound was 0.47; $[α]_D^{20} = +296°$ (c = 0.05 $CH_3OH$).

EXAMPLE 3

4'-deoxyadriamycin

A solution of 4'-deoxy-daunomycin prepared as described in Example 2 in a mixture of methanol and dioxane was treated with bromine to form the α 14-bromo-derivative. Treatment of the 14-bromo derivative with an aqueous solution of sodium formate at room temperature for 100 hours gave 4'-deoxy-adriamycin which was isolated as the hydrochloride; m.p. 163° (dec); $[α]_D^{20} = +320°$ (c = 0.05 $CH_3OH$) TLC on Merck Kieselgel HF buffered at pH 7 with phosphate M/15 using methylene chloride-methanol-water (10:2:02 v/v) solvent system Rf 0.13.

EXAMPLE 4

The condensation of compound II with the following anthracyclinones: 1,4-dimethyl-4-demethox-ydaunomycinone, 1,4-dichloro-4-demethoxydaunomycinone, 1,4-dibromo-4-demethoxydaunomycinone, 2,3-dimethyl-4-demethoxydaunomycinone, 2,3-dichloro-4-demethoxydaunomycinone, 2,3-dibromo-4-demethoxydaunomycinone, 1-methoxydaunomycinone in accordance with the procedure of Example 2 gives the corresponding 4'-deoxy-glycosides (daunomycin derivatives).

EXAMPLE 5

The daunomycin derivatives prepared in accordance with Example 4 can then be treated as in Example 3 to obtain the corresponding adriamycin derivatives.

Biological activity

The antitumor activity of a representative number of the novel antibiotic compounds of the invention (i.e., 4'-deoxydaunomycin and 4'-deoxy-adriamycin) was evaluated on several transplanted tumors in mice in comparison with the known antitumor agents daunomycin and adriamycin.

The results are given in the following tables.

$L_{1210}$ Leukemia

Inbred $BDF_1$ mice were intraperitoneally inoculated with $10^5$ leukemia cells/mouse and then treated intraperitoneally one day after the tumor inoculation with varying doses of the compounds under examination. The average survival time percentage and the number of long term survivors are given in Table 1.

TABLE 1

| | Action on $L_{1210}$ Leukemia | | | |
|---|---|---|---|---|
| Compound | Dose mg/kg | Average Survival Time (%) | Long Term Survivors (after 60 days) | Toxic Deaths |
| Daunomycin | 2 | 162 | — | — |
| | 4 | 162 | — | — |
| | 6 | 156 | — | 4/10 |
| 4'-Deoxy-daunomycin | 4 | 162 | — | — |
| | 8 | 187 | — | 1/10 |
| | 16 | 162 | — | 8/10 |
| Adriamycin | 2.5 | 145 | — | — |
| | 5 | 155 | 2/20 | — |
| | 10 | 163 | 2/20 | 3/18 |
| 4'-Deoxy-Adriamycin | 1 | 155 | — | — |
| | 2 | 162 | — | — |
| | 4 | 177 | 2/10 | — |
| | 5 | 133 | 1/10 | 6/10 |
| | 10 | 66 | — | 10/10 |

Transplanted Gross Leukemia

Inbred $C_3H$ female mice were intravenously inoculated with a suspension of Leukemia lymphonodes and spleen cells (2 × $10^6$ Leukemia cells/mouse) and treated intravenously on days 1,2 and 3 after inoculation with the compounds under examination. The average survival time percentage is given in Table 2.

TABLE 2

| | Action on Transplanted Gross Leukemia | | | |
|---|---|---|---|---|
| Compound | Dose mg/kg | Average Survival Time (%) | Long Term Survivors (after 45 days) | Toxic Deaths |
| Daunomycin | 3.5 | 128 | — | — |
| | 4.5 | 143 | — | — |
| | 5.5 | 171 | — | — |
| 4'-Deoxy-Daunomycin | 2 | 128 | — | — |
| | 4 | 157 | — | 2/10 |
| | 8 | 100 | — | 9/10 |
| Adriamycin | 3.5 | 183 | — | — |
| | 4.5 | 200 | — | — |
| | 5.5 | 216 | 3/10 | — |
| 4'-Deoxy-Adriamycin | 1.75 | 200 | — | — |
| | 2.25 | 233 | 1/10 | — |
| | 2.75 | 233 | — | 1/9 |

Ascites lymphocytic P$_{388}$ Leukemia

Male CDF$_1$ mice were intraperitoneally inoculated with 10$^6$ leukemia cells/mouse and treated intraperitoneally on the first day after inoculation with different doses of the compounds under examination. The average survival time percentage is given in Table 3.

TABLE 3

| Compound | Action on P$_{388}$ Leukemia | |
|---|---|---|
| | Dose mg/kg | Average Survival Time (%) |
| Adriamycin | 2.5 | 218 |
| | 5 | 209 |
| | 10 | 264 |
| 4'-Deoxy-Adriamycin | 2 | 204 |
| | 4 | 218 |
| | 6 | 236 |
| | 8 | 245 |

Solid Sarcoma 180

Swiss CD$_1$ mice were subcutaneously grafted with fragments of neoplastic (Solid Sarcoma 180) tissue and treated intravenously on days 1, 2, 3, 4 and 5 after inoculation with different doses of the compounds under examination. The growth of the tumors was evaluated by caliper measurement on the 11th day after the tumor implants. The results are given in Table 4.

TABLE 4

| Compound | Activity on Solid Sarcoma 180 | | |
|---|---|---|---|
| | Dose mg/kg | Weight Tumor gr. | T/C% |
| Adriamycin | 1.6 | 0.890 | 52 |
| | 2.0 | 0.875 | 51 |
| 4'-Deoxy-Adriamycin | 0.8 | 0.810 | 47 |
| | 1.0 | 0.790 | 46 |

Variations and modifications can, of course, be made without departing from the spirit and scope of the invention.

Having thus described our invention what we desire to secure by Letters Patent and hereby claim is:

1. A compound of the formula

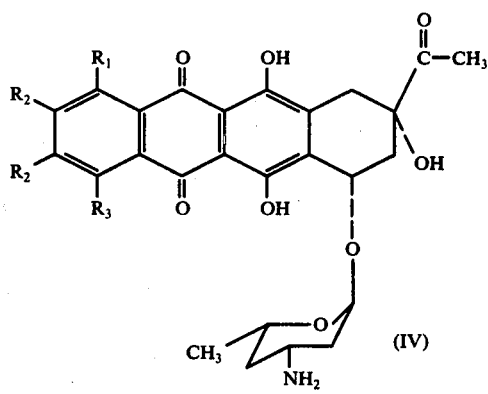

(IV)

wherein when
a. R$_1$ and R$_2$ are hydrogen, R$_3$ is a lower alkoxy group having from 1 to 4 carbon atoms; when
b. R$_2$ is hydrogen; R$_1$ and R$_3$ are both hydrogen, methyl, methoxy, chlorine or bromine; and when
c. R$_1$ and R$_3$ are hydrogen, R$_2$ is methyl, methoxy, chlorine or bromine.

2. A compound according to claim 1, which is 4'-deoxydaunomycin.

3. A compound according to claim 1, which is 1,4,-dimethyl-4-demethoxy-4'-deoxy-daunomycin.

4. A compound according to claim 1, which is 1,4-dichloro-4-demethoxy-4'-deoxy-daunomycin.

5. A compound according to claim 1, which is 1,4-dibromo-4-demethoxy-4'-deoxy-daunomycin.

6. A compound according to claim 1, which is 2,3-dimethyl-4-demethoxy-4'-deoxy-daunomycin.

7. A compound according to claim 1, which is 2,3-dichloro-4-demethoxy-4'-deoxy-daunomycin.

8. A compound according to claim 1, which is 2,3-dibromo-4-demethoxy-4'-deoxy-daunomycin.

9. A compound of the formula wherein when
a. R$_1$ and R$_2$ are hydrogen, R$_3$ is a lower alkoxy group having from 1 to 4 carbon atoms; when
b. R$_2$ is hydrogen; R$_1$ and R$_3$ are both hydrogen, methyl, methoxy, chlorine or bromine; and when
c. R$_1$ and R$_3$ are hydrogen, R$_2$ is methyl, methoxy, chlorine or bromine.

10. A compound according to claim 9, which is 4'-deoxy-adriamycin.

11. A compound according to claim 9, which is 1,4-dimethyl-4-demethoxy-4'-deoxy-adriamycin.

12. A compound according to claim 9, which is 1,4-dichloro-4-demethoxy-4'-deoxy-adriamycin.

13. A compound according to claim 9, which is 1,4-dibromo-4-demethoxy-4'-deoxy-adriamycin.

14. A compound according to claim 9, which is 2,3-dimethyl-4-demethoxy-4'-deoxy-adriamycin.

15. A compound according to claim 9, which is 2,3-dichloro-4-demethoxy-4'-deoxy-adriamycin.

16. A compound according to claim 9, which is 2,3-dibromo-4-demethoxy-4'-deoxy-adriamycin.

17. A method of inhibiting the growth of a tumor selected from the group consisting of L$_{1210}$ leukemia, transplated gross leukemia, lymphocytic P$_{388}$ leukemia and solid sarcoma 180 which comprises administering to a host afflicted with said tumor an amount of a compound according to claim 1 sufficient to inhibit the growth of said tumor.

18. A method according to claim 17, wherein said compound is administered intraperitoneally or intravenously.

19. A method of inhibiting the growth of a tumor selected from the group consisting of L$_{1210}$ leukemia, transplanted gross leukemia, lymphocytic P$_{388}$ leukemia and solid sarcoma 180 which comprises administering to a host afflicted with said tumor an amount of a compound according to claim 9 sufficient to inhibit the growth of said tumor.

20. A method according to claim 19, wherein said compound is administered intraperitoneally or intravenously.

21. A pharmaceutical composition comprising a therapeutically effective amount of a compound as claimed in claim 1 and an inert carrier therefor.

22. A pharmaceutical composition comprising a therapeutically effective amount of a compound as claimed in claim 9 and an inert carrier therefor.

* * * * *

UNITED STATES PATENT OFFICE
CERTIFICATE OF CORRECTION

Patent No. 4,067,969                    Dated January 10, 1978

Inventor(s) Sergio Penco et al

It is certified that error appears in the above-identified patent and that said Letters Patent are hereby corrected as shown below:

Column 5, line 38: "ajusted" should read -- adjusted --.

Column 7, Table 4, last column: "T/C %" should read -- *T/C % --; Table 4: Should have a footnote: -- *T/C - mean tumor weight of treated mice/mean tumor weight of control mice x 100. --.

Signed and Sealed this

Third Day of October 1978

[SEAL]

Attest:

RUTH C. MASON
Attesting Officer

DONALD W. BANNER
Commissioner of Patents and Trademarks